(12) United States Patent
Frasch et al.

(10) Patent No.: US 8,084,206 B2
(45) Date of Patent: Dec. 27, 2011

(54) HIGH SPEED, HIGH FIDELITY, HIGH SENSITIVITY NUCLEIC ACID DETECTION

(75) Inventors: Wayne Frasch, Phoenix, AZ (US); David Spetzler, Scottsdale, AZ (US); Justin York, Phoenix, AZ (US)

(73) Assignee: Arizona Board of Regents, a body corporate acting for and on behalf of Arizona State University, Scottsdale, AZ (US)

( * ) Notice: Subject to any disclaimer, the term of this patent is extended or adjusted under 35 U.S.C. 154(b) by 87 days.

(21) Appl. No.: 12/439,061

(22) PCT Filed: Aug. 29, 2007

(86) PCT No.: PCT/US2007/077128
§ 371 (c)(1),
(2), (4) Date: Aug. 14, 2009

(87) PCT Pub. No.: WO2008/027977
PCT Pub. Date: Mar. 6, 2008

(65) Prior Publication Data
US 2010/0015616 A1   Jan. 21, 2010

Related U.S. Application Data

(60) Provisional application No. 60/841,007, filed on Aug. 30, 2006.

(51) Int. Cl.
*C12Q 1/68* (2006.01)
*C12P 19/34* (2006.01)

(52) U.S. Cl. .................................... 435/6.1; 435/91.2

(58) Field of Classification Search ............. 435/6, 91.2, 435/6.1
See application file for complete search history.

(56) References Cited

U.S. PATENT DOCUMENTS

| | | | |
|---|---|---|---|
| 6,593,086 B2 * | 7/2003 | Zhang | 435/6 |
| 2003/0119004 A1 | 6/2003 | Wenz et al. | |
| 2004/0185443 A1 * | 9/2004 | Dahl | 435/6 |

* cited by examiner

*Primary Examiner* — Gary Benzion
*Assistant Examiner* — Cynthia Wilder
(74) *Attorney, Agent, or Firm* — Citadel Patent Law; George A. Leone

(57) ABSTRACT

The present invention provides methods, compositions, and kits for nucleic acid detection.

12 Claims, 6 Drawing Sheets i. Complimentary ii. Noncomplimentary

SEQUENCE LISTING

<160> NUMBER OF SEQ ID NOS: 6

<210> SEQ ID NO 1
<211> LENGTH: 40
<212> TYPE: DNA
<213> ORGANISM: Artificial
<220> FEATURE:
<223> OTHER INFORMATION: Synthetic

<400> SEQUENCE: 1
aatgctaggc tcgacctagc atcggcgaat cgcatcaggc    40

<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
ttacgatccg agctggatcg    20

<210> SEQ ID NO 3
<211> LENGTH: 20
<212> TYPE: DNA
<213> ORGANISM: Artificial
<220> FEATURE:
<223> OTHER INFORMATION: Synthetic

<400> SEQUENCE: 3
tagccgctta gcgtagtccg    20

<210> SEQ ID NO 4
<211> LENGTH: 40
<212> TYPE: DNA
<213> ORGANISM: Artificial
<220> FEATURE:
<223> OTHER INFORMATION: Synthetic

<400> SEQUENCE: 4
ttacgatccg agctggatcg tagccgctta gcgtagtccg    40

<210> SEQ ID NO 5
<211> LENGTH: 40
<212> TYPE: DNA
<213> ORGANISM: Artificial
<220> FEATURE:
<223> OTHER INFORMATION: Synthetic

<400> SEQUENCE: 5
aatgctaggc tcgacctaga atcggcgaat cgcatcaggc    40

<210> SEQ ID NO 6
<211> LENGTH: 40
<212> TYPE: DNA
<213> ORGANISM: Artificial
<220> FEATURE:
<223> OTHER INFORMATION: Synthetic

<400> SEQUENCE: 6
ttacgatccg agctggatct tagccgctta gcgtagtccg    40

HIGH SPEED, HIGH FIDELITY, HIGH SENSITIVITY NUCLEIC ACID DETECTION

CROSS REFERENCE

This application claims priority to U.S. Provisional Patent Application Ser. No. 60/841,007 filed Aug. 30, 2006, incorporated by reference herein in its entirety.

STATEMENT OF GOVERNMENT INTEREST

Financial assistance for this project was provided by U.S. Government, DARPA #N66001-03-C-XXXX; thus the United States Government may have certain rights to this invention.

BACKGROUND OF THE INVENTION

Rapid and sensitive biosensing of nucleic acids or proteins is vital for the identification of pathogenic agents of biomedical and bioterrorist importance, providing forensic evidence, and for diagnoses of genetic diseases, among other uses. Development of methods that do not require target-amplification systems like polymerase chain reaction (PCR) that increase the complexity of the determination and the potential for error are a major challenge. Surface-enhanced Raman scattering to detect a silver coating built up on patches of several thousand immobilized target DNA molecules bound to gold nanoparticles has been used to detect target DNA at concentrations as low as 20 femtomolar, and is among the most sensitive means to detect DNA (ref (3-6)). However, these methods are limited by nonspecific binding, hybridization kinetics, and extensive incubation times. These technologies all require the binding of several thousand DNA-bound reporter groups as an aggregate to obtain a detectable signal. The ultimate goal is to achieve a detectable signal for each DNA molecule. Detection of a molecule with a specific sequence necessarily depends upon hybridization of the target with a probe DNA molecule, and upon the target-dependent assembly of a molecular detection probe such as a nanoparticle. Consequently, with single molecule biosensing, the detection limit becomes dependent on the statistical difference between target-specific and nonspecific binding events.

SUMMARY OF THE INVENTION

In a first aspect, the present invention provides methods for detecting a target nucleic acid, comprising:

(a) contacting a plurality of target-specific nucleic acid probes that are each complementary to a target nucleic acid, to a sample under conditions whereby the plurality of target-specific nucleic acid probes hybridize to the target nucleic acid if the target nucleic acid is present in the sample, wherein upon hybridization to the target nucleic acid, the target-specific nucleic acid probes form a series of target-specific nucleic acid probes directly adjacent to one another, wherein a first target specific nucleic acid probe is capable of binding or is bound to a molecular post and a second target-specific nucleic acid probe is capable of binding or is bound to a detection probe, and wherein the first target-specific nucleic acid probe and the second target-specific nucleic acid probe are positioned at the 5' and 3' end, respectively, of the series of target specific nucleic acid probes;

(b) optionally binding the molecular post to the first target-specific nucleic acid probe and/or binding the detection probe to the second target-specific nucleic acid probe if the molecular post and/or detection probe were not bound prior to hybridization;

(c) ligating the series of target-specific nucleic acid probes together to produce a ligation product;

(d) optionally binding the molecular post to the first target-specific nucleic acid probe and/or binding the detection probe to the second target-specific nucleic acid probe if the molecular post and/or detection probe were not bound prior to ligation;

(e) treating the ligation product with one or both of:
  (i) exonuclease digestion; and
  (ii) denaturation to create all single stranded bridges after ligation;

(f) binding the molecular post to the first target-specific nucleic acid probe and/or binding the detection probe to the second target-specific nucleic acid probe if the molecular post and/or detection probe were not bound prior to the step (e) treatment; and (g) detecting the ligation product.

In another aspect, the invention provides kits for nucleic acid detection comprising a plurality of target-specific nucleic acid probes that are each complementary to a target nucleic acid, wherein upon hybridization to the target nucleic acid the plurality of target-specific nucleic acid probes will be directly adjacent to each other; wherein a first target specific nucleic acid probe is capable of binding or is bound to a molecular post and a second target-specific nucleic acid probe is capable of binding or is bound to a detection probe, and wherein the first target-specific nucleic acid probe and the second target-specific nucleic acid probe are positioned at the 5' and 3' end, respectively, of the series of target specific nucleic acid probes.

In another aspect, the present invention provide composition comprising a plurality of target-specific nucleic acid probes that are each complementary to a target nucleic acid, wherein upon hybridization to the target nucleic acid the plurality of target-specific nucleic acid probes will be directly adjacent to each other; wherein a first target specific nucleic acid probe is bound to a first affinity tag capable of binding to a molecular post and a second target-specific nucleic acid probe is bound to a second affinity tag capable of binding to a detection probe, and wherein the first target-specific nucleic acid probe and the second target-specific nucleic acid probe are positioned at the 5' and 3' end, respectively, of the series of target specific nucleic acid probes.

In a further aspect, the present invention provides compositions comprising:

(a) a solid support; and
(b) a plurality of molecular posts attached to the solid support, wherein the plurality of molecular posts comprise an affinity target for binding to a specific affinity tag.

DETAILED DESCRIPTION OF THE INVENTION

Figure 1:
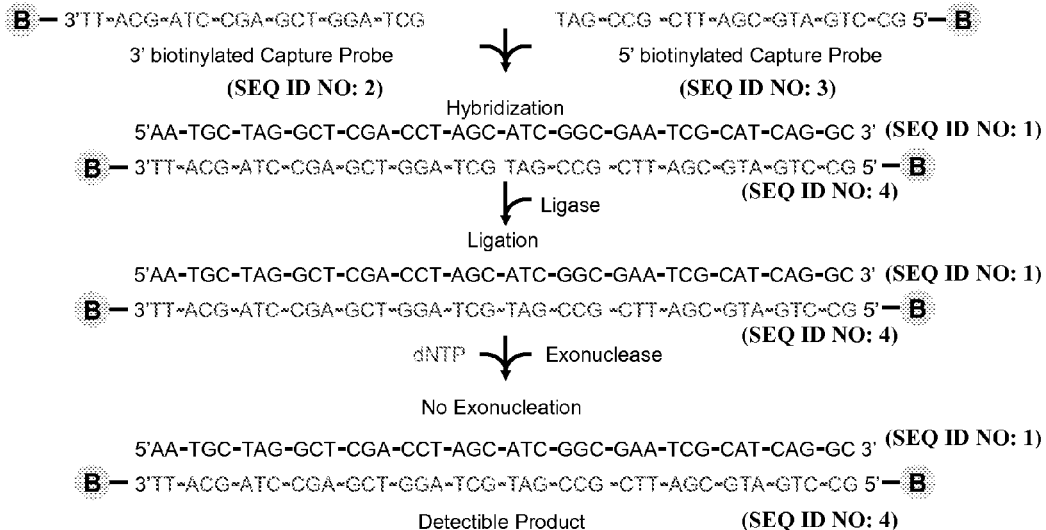
FIG. 1. Stepwise LXR reactions and products when target and probes are (i) complementary and (ii) contain a SNP.
Figure 1:
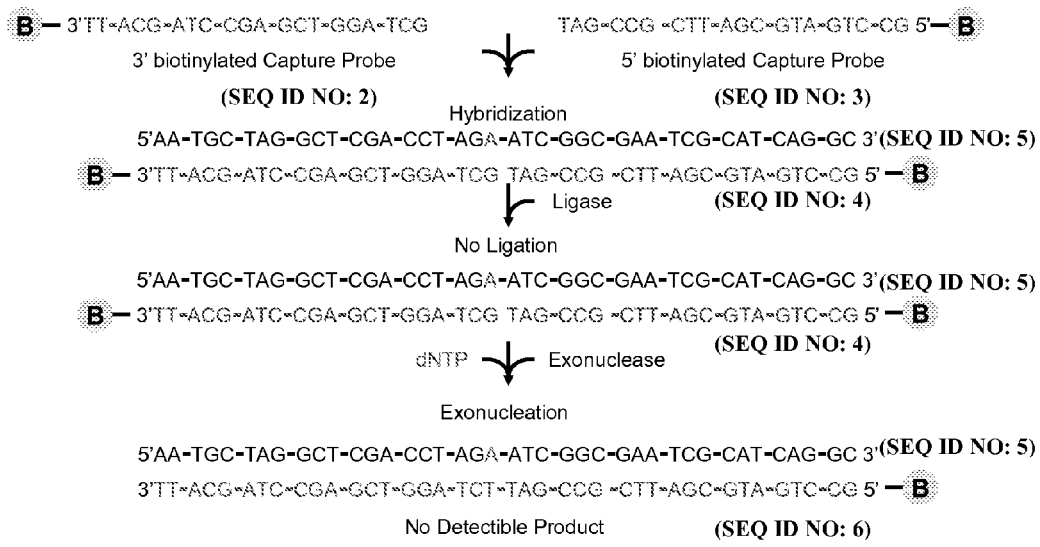

In a first aspect, the present invention provides methods for detecting a target nucleic acid, comprising:

(a) contacting a plurality of target-specific nucleic acid probes that are each complementary to a target nucleic acid, to a sample under conditions whereby the plurality of target-specific nucleic acid probes hybridize to the target nucleic acid if the target nucleic acid is present in the sample, wherein upon hybridization to the target nucleic acid, the target-specific nucleic acid probes form a series of target-specific nucleic acid probes directly adjacent to one another, wherein a first target specific nucleic acid probe is capable of binding or is bound to a molecular post and a second target-specific nucleic acid probe is capable of binding or is bound to a detection probe, and wherein the first target-specific nucleic acid probe and the second target-specific nucleic acid probe are positioned at the 5' and 3' end, respectively, of the series of target specific nucleic acid probes;

(b) optionally binding the molecular post to the first target-specific nucleic acid probe and/or binding the detection probe to the second target-specific nucleic acid probe if the molecular post and/or detection probe were not bound prior to hybridization;

(c) ligating the series of target-specific nucleic acid probes together to produce a ligation product;

(d) optionally binding the molecular post to the first target-specific nucleic acid probe and/or binding the detection probe to the second target-specific nucleic acid probe if the molecular post and/or detection probe were not bound prior to ligation;

(e) treating the ligation product with one or both of:
  (i) exonuclease digestion; and
  (ii) denaturation to create all single stranded bridges after ligation;

(f) binding the molecular post to the first target-specific nucleic acid probe and/or binding the detection probe to the second target-specific nucleic acid probe if the molecular post and/or detection probe were not bound prior to the step (e) treatment; and (g) detecting the ligation product.

In a specific embodiment, step (e) comprises treating the ligation product with exonuclease.

The methods disclosed herein can detect very small numbers of individual molecules of a nucleic acid target via ligation events with the target-specific nucleic acid probes, which are ligated only in the presence of the nucleic acid target, producing fully constructed ligated products comprising a molecular post and a detection probe. The detection probe reveals the presence of the bridging ligated product that is indicative of the nucleic acid target. The exonuclease step ensures that only perfectly paired target-specific nucleic acid probes are hybridized to the target nucleic acid. As a result, amplification steps such as ligation chain reaction (LCR) are not necessary, although may be useful, as described below. When excluding an LCR step, ligation of the target-specific nucleic acids can be carried out using any ligase (as opposed to the requirement for thermal stable ligase, for example Taq ligase, on LCR products), thus permitting a much wider range of ligation conditions to be used.

In the absence of an exonuclease digestion step, nonspecific hybridization can produce an equal number of viable bridges as perfectly complementary targets that get ligated. The inclusion of an exonuclease digestion removes the ligand at the 3' end, thus eliminating the ability for the DNA to assemble with both the post and the detection probe. Thus, inclusion of an exonuclease digestion step greatly improves the ability to detect target. Additionally, when amplification is used the error rates of the reaction increase as a function of the number of cycles (error rate for one cycles $*2^{number\ of\ cycles}$). The combination of a ligation reaction followed by an exonuclease digestion is referred to as LXR in the rest of this document. Thus the LXR reaction taught here has an error rate that is $2^x$ times better than the error rate of LCR. The inclusion of the exonuclease step also allows the number of complementary sequences to be compared to the nonspecific background binding of the detection probe, where as with LCR or PCR, the number of complementary probes must be compared to the number of hybridized probes, which is orders of magnitude greater than the nonspecific binding of the detection probe alone.

Finally, since inclusion of the exonuclease step makes the reaction much more specific, it facilitates conducting the reactions in unpurified samples, including but not limited to crude cell lysate.

For all of these reasons, the present methods, with the inclusion of an exonuclease step, result in a far superior detection method than prior art detection techniques.

In an alternative embodiment, the exonuclease step can be replaced through or accompanied by denaturation using a denaturing agent (including but not limited to heat and NaOH treatment) to create all single stranded bridges after ligation, and thus to ensures that only perfectly paired target-specific nucleic acid probes are hybridized to the target nucleic acid.

The sample from which detection of the target nucleic acid is made can be any sample of interest, including but not limited to synthetic nucleic acids, genomic DNA, cell lysates, tissue homogenates, forensic samples, environmental samples, and isolated nucleic acid samples from cells, tissues, or complete organisms.

The target nucleic acid can be any nucleic acid that can serve as a bridge between a molecular post and a detection probe to detect construction of the device and for which the means of formation of that bridge is specific to that target nucleic acid. Thus, the target nucleic acid can comprise DNA or RNA and can be single stranded or double stranded. In a specific embodiment, the target nucleic acid is double stranded. In a more specific embodiment, the target nucleic acid is a double stranded DNA.

The plurality of target specific nucleic acid probes can be any 2 or more nucleic acid sequences that are complementary to directly adjacent sequences on the same target nucleic acid. There is no other specific nucleic acid sequence requirement for the plurality of target specific nucleic acids. The plurality of target specific nucleic acid probes can independently comprise DNA or RNA and can be single stranded or double stranded. In a specific embodiment, the target specific nucleic acid probes are single stranded. In a more specific embodiment, the target specific nucleic acid probes are single stranded DNA. In a further specific embodiment, the plurality of target-specific nucleic acids probes comprise or consist of 3, 4, 5, 6, 7, 8, 9, 10, or more target-specific nucleic acids probes.

There are significant benefits in using multiple target-specific nucleic acid probes. Specifically, each target-specific nucleic acid has an error rate that is associated with it; say for example $10^{-4}$, since each target-specific nucleic acid must engage in a successful ligation to avoid being degraded by the exonuclease. The error rate for a multi-target-specific nucleic acid probe ligation is the product of the error rate for each individual target-specific nucleic acid. For example, if 5 target-specific nucleic acids probes were used, then the total error rate would be $(10^{-4})^5 = 10^{-20}$. Furthermore, the ligase reaction is most sensitive to mismatches within 3 bases from the site of ligation in the 3' direction, thus mismatches that are >3 bases away from the site of ligation are unlikely to be detected. By using multiple target-specific nucleic acid probes, the ligation reaction can be sensitive to longer stretches of bases. For example, if each ligation site were 6 bases away from each other, then all 6 bases in between would have to be complementary for the probes to be ligated together. Thus increasing the number of target-specific nucleic acid probes has the additional effect of increasing specificity of binding to longer target sequences. In the event that the target nucleic acid is in a sample that contains similar nucleic acid sequences that differ at a few non-adjacent nucleotides, it is possible that 2 target-specific nucleic acids probes would not be sufficient for detection.

The preferred number of target-specific nucleic acids for detection of a given specific nucleic acid target is dependent upon the target nucleic acid that is being detected and can be determined by those skilled in the art based upon the teachings herein.

As used herein the term "directly adjacent" means juxtaposed 5' phosphate and 3' hydroxyl termini of two adjacent target-specific nucleic acid probes hybridized to the complementary target nucleic acid, which can be ligated together by the action of a nucleic acid ligase.

Optimization of conditions for contacting the plurality of target-specific nucleic acid probes to a sample under conditions whereby the plurality of target-specific nucleic acid probes hybridize to the target nucleic acid if the target nucleic acid is present in the sample can be readily accomplished by those of skill in the art. The hybridization conditions are thus optimized to limit hybridization/ligation to those situations where the target nucleic acid is present. Such optimization includes consideration of the target-specific nucleic acid probe sequence, number, and length, reaction buffer, reaction temperature, and reaction time. The specific hybridization conditions used will depend on the length of the target-specific nucleic acid probes employed, their GC content, as well as various other factors as is well known to those of skill in the art. Non-limiting exemplary conditions can be found, for example, at the web site epicentre.com, by selecting "technical resources-protocols", then accessing "SNP & Mutation Discovery & Screening", then selecting the "Ampliqase Thermostable DNA Ligase" pdf file. The inclusion of an exonuclease digestion step in the methods of the invention to degrade non-complementary hybridized nucleic acid sequences reduces the stringency requirements for successful reactions.

As used herein, the term "molecular post" means any biological or synthetic molecular structure capable of binding to the first target-specific nucleic acid probes (directly or indirectly), and that permits detection. The size of the molecular post is not a critical feature of the invention, however it is preferred that the post be of nanoscale dimensions. By keeping the post on that scale, the detection probes will all be at approximately the same z-axis position. Thus, when performing, for example, optical detection, a single focal plane will encompass all of the specifically bound detection probes. In one specific embodiment, the molecular post comprises a biomolecule, including but not limited to $F_1$-ATPases, actomyosin, ciliary axonemes, bacteria flagellar posts, kinesin/microtubules, and nucleic acid helicases and polymerases. In another specific embodiment, the molecular post comprises a magnetic particle. When using a magnetic particle as the post, the post should be small enough to allow the detection probe to be visible. Further non-limiting examples of suitable molecular posts include synthetics materials, metals, silicone based posts, plastics, carbon structures, and lipid structures.

As used herein, the "detection probe" is anything that is capable of binding to the second target-specific nucleic acid probe (directly or indirectly), and which provides a means of detecting the presence of the resulting ligation product, such as metallic nanoparticles (rods, spheres, quantum dots, etc.) fluorescent dyes, and nanoparticles labeled with fluorescent dyes. When the detection probe comprises a metallic nanoparticle and the molecular post is a magnetic particle, it is preferred that the metallic nanoparticle detection probe be non-magnetic (for example, silver or gold). In a specific embodiment, elemental metal nanorods are used as the detection probe, including but not limited to gold, silver, aluminum, platinum, copper, zinc, and nickel. In one example, gold rod detection probes capable of visual observation by microscope are attached to the second target-specific nucleic acid probe through a biotin-avidin bond. In a further example, the gold nanorod is coated with anti-DIG antibody (the affinity target), which binds specifically to a DIG (Digoxigenin) second affinity tag.

The molecular post and the detection probe can be bound to the first and second target-specific nucleic acid probes either directly or indirectly. In various specific embodiments, the molecular post is indirectly bound to the first target-specific nucleic acid probe via a first affinity tag and/or the detection probe is indirectly bound to the second target-specific nucleic acid probe via a second affinity tag. In these embodiments, the first affinity tag and the second affinity tag may be the same or different as is most suitable for their ultimate attachment to the specific molecular post and the detection probe employed.

The first affinity tag can bind to the molecular post and the second affinity tag can bind to the detection probe either directly (for example by a covalent bond between the target-specific nucleic acid probe and the affinity tag) or indirectly through another molecule. In a specific embodiment, the first and/or second affinity tags bind indirectly to the molecular post and the detection probe, respectively. In this specific embodiment, the affinity tag binds directly to the target-specific nucleic acid probe and to an affinity target, wherein the affinity target is bound to the molecular post or the detection probe. Together, an affinity tag and affinity target make up a binding pair. Either member of a binding pair can be used as an affinity tag and either member can be used as an affinity target. An affinity target includes both separate molecules and portions of molecules, such as an epitope of a protein that interacts specifically with an affinity tag. Antibodies, either member of a receptor/ligand pair, and other molecules with specific binding affinities can be used as affinity tags. Binding an affinity tag to the target-specific nucleic acid probes thus permits an indirect linkage between the target-specific nucleic acid probes and the molecular post or the detection label. An affinity tag that interacts specifically with a particular affinity target is said to be specific for that affinity target. For example, an affinity tag which is an antibody that binds to a particular antigen is said to be specific for that antigen. Complementary nucleotide sequences can also be used as binding pairs.

A non-limiting example of a binding pair is biotin/avidin. Other non-limiting binding pair examples include digoxigenin (DIG)/anti-digoxigenin antibody and other antigen/antibody pairs. Epitope tags, such as his-tags, and antibodies directed against the epitope tag (or fragments thereof) are further examples of binding pairs for use with the methods of the present invention. Those of skill in the art will understand that certain embodiments listed herein as indirect binding of the affinity tag and the molecular post or detection probe can also be used for direct binding embodiments. For example, where the second affinity tag is an epitope tag as described above, the detection probe can be a labeled antibody against the epitope tag. Many further such examples will be readily apparent to those of skill in the art.

The affinity tags are bound to the first and last target-specific nucleic acid probes so as to not interfere with the ability of the series of target-specific nucleic acid probes to be ligated together after hybridization to the target nucleic acid. In a specific embodiment, one of the affinity tags is bound at or near the 5' end of one of the target specific nucleic acid probes, and the other affinity tag is bound at or near the 3' end of the other target-specific nucleic acid probe, so as to permit juxtaposition of the 5' phosphate and 3' hydroxyl termini of the adjacent target-specific nucleic acids at the desired sites of ligation after hybridization of the target-specific nucleic acid probes to the target nucleic acid. Such design of the target-specific nucleic acid probes and the affinity tags is well within the level of skill of those in the art.

Prior to hybridization to the target nucleic acid, the first target specific nucleic acid probe is capable of binding or is bound to a molecular post and a second target-specific nucleic acid probe is capable of binding or is bound to a detection probe. Thus, the hybridization may occur with (a) the first target-specific nucleic acid probe being bound to the molecular post, (b) the second target-specific nucleic acid probe bound to the detection probe, (c) both being bound, or (d) neither being bound. In those embodiments where the molecular post and/or detection probe are not bound to the appropriate target-specific nucleic acid probe prior to hybridization, they are bound at a later step, either after hybridization but prior to ligation; after ligation; or after the exonuclease digestion and/or denaturation step (see below). Based on the teachings herein, it will be apparent to those of skill in the art how to choose the appropriate stage of the method to carry out binding of the molecular post to the first target-specific nucleic acid probe and the detection probe to the second target-specific nucleic acid probe for different experimental designs. For example, when the molecular post comprises a magnetic particle, it is preferable to bind the detection probe to the second target-specific nucleic acid prior to hybridization. This ensures that each side of the bridge binds to the appropriate group, either the magnetic bead or the reporter group. In embodiments where the molecular post and the detection probe are both bound to the target-specific nucleic acid probes indirectly via affinity tags, and the same affinity tag is used for both, then it is preferred for at least one of the molecular post and the detection probe to be bound to the target-specific nucleic acid probe prior to hybridization. This is to ensure that there are not any bridges that have reporter groups or magnetic beads on both sides: the only possibility is that one side has a magnetic bead and the other side has the reporter group. In embodiments where different affinity tags are used, then the molecular post and the detection probe can be bound at any appropriate step as noted above.

When a non-magnetic particle is used as the molecular post, it is preferably bound to the first target-specific nucleic acid probe after ligation and exonuclease digestion and/or denaturation. This is to minimize the interactions of the reporter group with the enzymes, as such interactions can reduce the efficiency of the enzymatic reactions. As will thus be apparent to those of skill in the art, binding of the molecular post and the detection probe to the target-specific nucleic acid probes can be done at any point of the process (depending on how the procedure is designed), so long as care is taken to ensure that only the desired binding occurs.

As will be understood by those of skill in the art, the LXR reactions are allowed to proceed as efficiently as possible, while ensuring that the correct group is bound to each end of the DNA bridge. If different moieties are used for the detection probe and molecular post, then it is preferable to bind the two after the exonuclease digestion and/or denaturation, so they do not interfere with the enzymes. If the same moiety is used for both the detection probe and molecular post, one of the two is preferably bound prior to hybridization. In this case it is preferable to bind the most inert group; while the linkage is the same, the groups that are being linked to are different. (For example, avidin-biotin is used to bind a gold nanoparticle on one side, and a magnetic bead on the other), and thus one group is more inert than the other.

In a further non-limiting example, a "moiety" on an accessible component of the molecular post can be designed, such as a cysteine residue created by site-directed mutagenesis at a specific position of a protein-based biomolecular post, such as the $\gamma$ subunit of F1-ATPase. The first affinity tag can be attached to the cysteine residue through linkage to its sulfhydryl group. Alternatively, an affinity target can be used to coat the molecular post, and can interact with the affinity tag. This molecular post coated with affinity targets can then be linked specifically to the affinity tag on the first target-specific nucleic acid. As will be apparent to those of skill in the art, site directed mutagenesis can be used to introduce a cysteine residue (or other useful residues) to various protein-based biomolecular posts so that they can be linked to affinity tags. Furthermore, there are a variety of covalent modification reagents that can modify specific amino acid side chains, as is known to those of skill in the art.

In some cases it is preferred that the molecular post is immobilized (i.e. secured in place) for detection. For example, it may be preferred to immobilize the molecular post for some rotation visualization techniques or if the detection depends on the perturbation of the local environment, such as micro current or impendence.

A series of molecular posts, either identical or two or more different molecular posts, can be immobilized on a surface to generate a molecular post array. If each post is coated with different affinity targets and different first target-specific nucleic acid probes (specific to the same or different target nucleic acids) are labeled with different affinity tags, this molecular post array can be used to detect multiple target nucleic acids in a manner similar to use of a gene chip. As used herein, an "array" comprises a solid surface, with molecular posts attached to said surface. Arrays typically comprise a plurality of molecular posts linked to different capture groups that are coupled to a surface of a substrate in different, known locations. For example, there are several silane derivatives to attach a variety of functional groups to a glass surface. The term "solid surface" as used herein refers to a material having a rigid or semi-rigid surface. Such materials will preferably take the form of chips, plates, slides, cover slips, small beads, pellets, disks or other convenient forms, although other forms may be used. The surfaces are generally coated with an affinity target. Such solid surfaces can be coated in any way that improves desired binding to its surface and/or minimizes non-specific binding to its surface. In a specific embodiment, nickel-nitrilotriacetic acid (Ni-NTA) affinity resin (Sigma-Aldrich product #P6611) is used. In a further embodiment, acetylated BSA can be added to reduce non-specific binding.

The ligation step of the methods of the invention can be accomplished by techniques known to those of skill in the art using commercially available nucleic acid ligases. Any DNA ligase is suitable for use in the disclosed methods. Preferred ligases are those that preferentially form phosphodiester bonds at nicks in double-stranded DNA. That is, ligases that fail to ligate the free ends of single-stranded DNA at a significant rate are preferred. Thermostable ligases are especially preferred. Many suitable ligases are known, such as T4 DNA ligase (Davis et al., Advanced Bacterial Genetics—A Manual for Genetic Engineering (Cold Spring Harbor Laboratory, Cold Spring Harbor, N.Y., 1980)), *E. coli* DNA ligase (Panasnko et al., J Biol. Chem. 253:4590-4592 (1978)), AMPLIGASE® (Kalin et al., Mutat Res., 283(2):119-123 (1992); Winn-Deen et al., Mol Cell Probes (England) 7(3): 179-186 (1993)), Taq DNA ligase (Barany, Proc. Natl. Acad Sci. USA 88:189-193 (1991), *Thermus thermophilus* DNA ligase (Abbott Laboratories), *Thermus scotoductus* DNA ligase and *Rhodothermus marinus* DNA ligase (Thorbjamardottir et al., Gene 151:177-180 (1995)). T4 DNA ligase is preferred for ligations involving RNA target sequences due to its ability to ligate DNA ends involved in DNA:RNA hybrids (Hsuih et al., Quantitative detection of HCV RNA using novel ligation-dependent polymerase chain reaction, American Association for the Study of Liver Diseases (Chicago, Ill., Nov. 3-7, 1995)). In another embodiment, modified nucleic acid probes can be used that allow adjacent nucleic acid probes to self ligate (see, for example, U.S. Pat. No. 7,033,753; Silverman et al., Nucleic Acids Research 2005, 33, 4978-4986).

While not required by the methods of the invention, the use of LCR in connection with the methods can be useful. Specifically, LCR can decrease the background and eliminate some false positives, depending upon the initial amount of target. Thus, in a further embodiment, ligation is accomplished by use of a ligation chain reaction. The term "ligation chain reaction" ("LCR") describes the process pioneered by Landegren et al. (1988 Science 241, 1077-1080). This process detects the presence of given DNA sequences based on the ability of probes to anneal directly adjacent to each other on a complementary target DNA molecule. The probes are then joined covalently by the action of a DNA ligase, provided that the nucleotides at the junction are correctly base-paired. Thus multiple single nucleotide substitutions can be distinguished. This strategy permits the rapid and standardized identification of gene sequences in genomic DNA, using single molecule FRET as a detection method (M. Wabuyele, H. Farquar, W. Stryjewski et al., JACS 125, 6937-6945 (2003)). In this method, the concentration of the solution is controlled so that only one molecule can be present in the volume of the detection cell. Due to its high specificity, LCR can be performed in crude samples, without the need for purifying the nucleic acid target, which significantly simplifies the assay process. The methods of the present invention have as one advantage the ability to detect multiple target nucleic acids simultaneously at single molecule detection level.

In a further embodiment, the disclosed method may use target dependent DNA ligation reactions (Cheng et al., 1996) to generate a ligation product with affinity tags on both ends so that it can serve as a bridge between the molecular post and the detection probe (the "fully assembled" ligation product). Ligation reaction requires the formation of juxtaposed 5' phosphate and 3' hydroxyl termini of adjacent target-specific nucleic acid probes, which are hybridized to a complementary nucleic acid target. The ligation will occur only if the target-specific nucleic acid probes are perfectly paired to the target nucleic acid and have no gaps between them. In the event that the sequences are not perfectly complimentary and ligation does not occur, there can still be a detectable bridge that is held together by the hydrogen bonds formed during hybridization, depending upon the initial starting concentration of the target. The exonuclease and/or denaturation step degrades this type of false positive, thereby increasing the accuracy of the reaction and permitting the detection of single nucleotides polymorphisms. Thus, the inclusion of the exonuclease digestion and/or denaturation after the LCR changes the error rate and the specificity of the reaction. Certain false positives will be eliminated by inclusion of the exonuclease and/or denaturation step. For example, if you have 1 target molecule and run enough cycles to produce 1000 bridges, it would appear the same as if you had 1000 targets that could hybridize but not ligate. The only way to differentiate these two cases is using the exonuclease and/or denaturation step.

In a non-limiting example, LCR conditions employed include an initial hybridization step at 95° C. for two minutes, followed by 19 cycles of 1 minute at 95° C. and 4 minutes at 65° C. in the presence of a thermostable DNA ligase and appropriate reaction components. Those of skill in the art are well-versed in modifying such cycling conditions to provide optimal hybridization and ligation based on the use of different nucleic acid sequences or different buffer conditions.

Following ligation, the sample is treated with exonuclease and/or denaturation to remove any imperfectly paired ligation products. A non-limiting example of an exonuclease step is to increase the temperature of the mixture of target and probe to 95° C., and then cool it to 45° C. The ligation buffer, 330 mM Tris-acetate (pH 7.8), 660 mM potassium acetate, 100 mM magnesium acetate and 5 mM DTT, 1 mM ATP, and enzyme can then be added to the sample to perform the ligation. The reaction time is a function of the ratio of DNA to the amount of enzyme added and can occur in a few minutes. The exonuclease reaction can then be run using a reaction buffer of 50 mM Tris-HCl, 10 mM $(NH_4)_2SO_4$, 10 mM $MgCl_2$, 4 mM dithiothreitol, and pH 7.5@25° C. when using phi29 DNA polymerase (see, for example, the web site neb.com/nebecomm/MSDSFiles/msdsM0269.pdf). DNA Polymerase Phi29 is the preferred enzyme to perform the exonuclease reaction as it has the largest strand displacement activity that we are aware of, and therefore allows the longest nucleotide sequence to be detected. However, any polymerase has the potential to be used for this step. The amount of time required for this step is a function of the ratio of DNA to enzyme and can be accomplished in a few minutes.

The methods of the invention further comprise detecting the ligation product following the product formation step. Such detection can be by any means suitable for detecting the ligation products, including but not limited to fluorescence microscopy, surface plasmon resonance, gel electrophoresis, calorimetric shifts, electric conductivity and autoradiography. Each of these detection techniques are well within the level of skill in the art.

Figure 3:
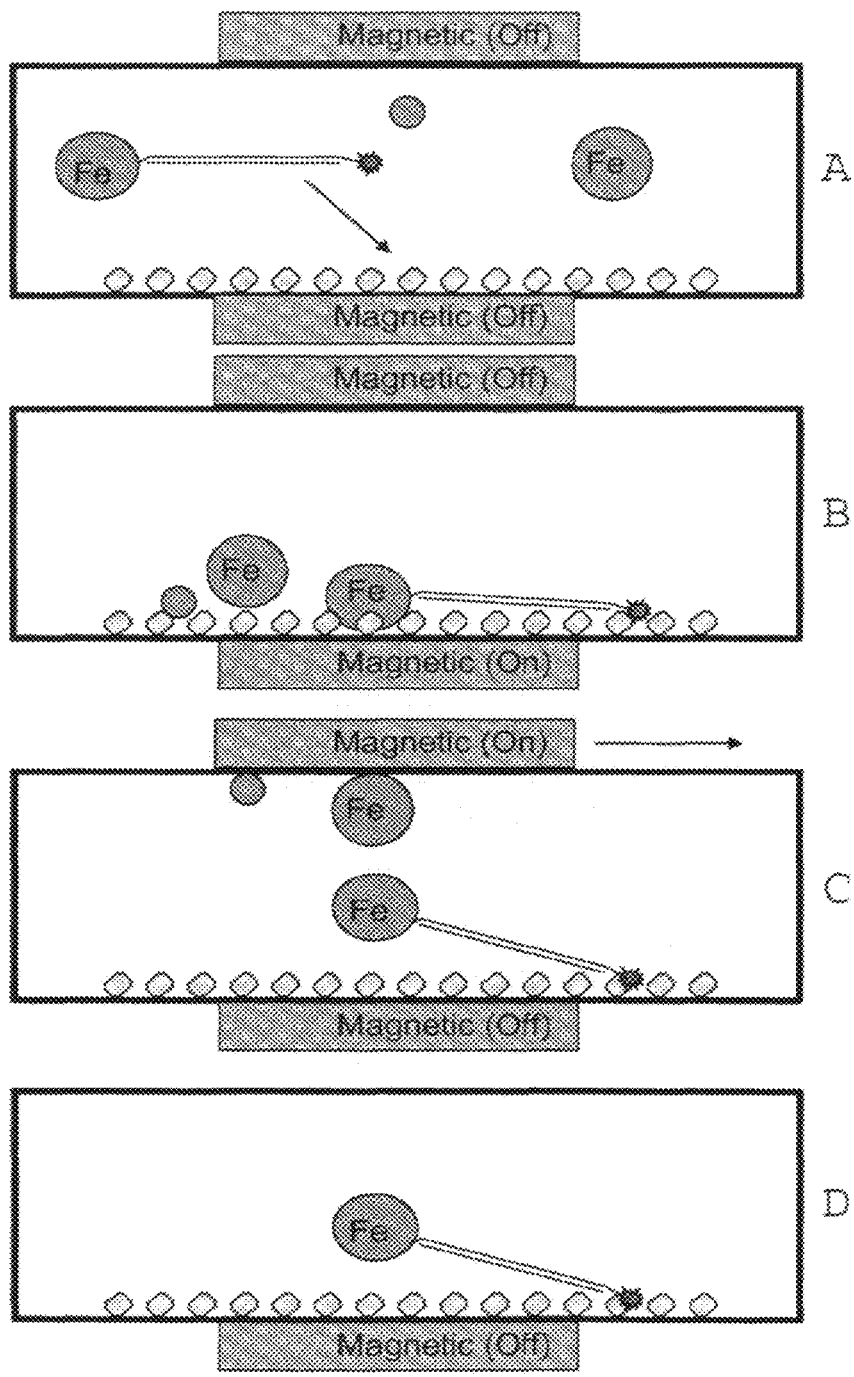
FIG. 3A-3D. Schematic of embodiments using magnetic particles.

In embodiments using a magnetic particle as the molecular post, a magnetic field can be applied and varied, to differentiate specifically bound detection probes from non-specifically bound detection probes, resulting in movement of the detection probe bound via the ligation product to the magnetic particle, thus confirming target dependent association of the magnetic particle with the detection probe. See, for example, FIG. 3. In one embodiment, the ligation product has a magnetic bead bound to one end and an affinity probe on the other (FIG. 3A). A first magnetic field is induced to pull the ligation product to a surface that is functionalized in such a manner as to bind to the affinity probe (for example, via an avidin-biotin interaction) (FIG. 3B). In a specific embodiment, the magnetic field is applied to the ligation product in solution, to pull it to a surface. In a further embodiment, the ligation product is formed on a surface, and the magnetic field pulls the ligation product to (a) a separate region of the surface; or (b) a second surface. The first magnetic field is turned off and a second magnetic field is used to remove any free magnetic particles (not bound to the surface) that did not have the affinity probe to hold them to the functionalized surface (FIG. 3C-D). The presence of the ligation product at the surface can be detected by measuring the changes in the magnetic field due to the presence of the remaining magnetic particles, or using microscopy.

Ligation product detection includes, but is not limited to, determining the number of ligation products present in the sample (to provide a number of copies of the target nucleic acid in the sample). When multiplex analysis is conducted, the detection step preferably includes the separate detection of the different detection probes (each specific for a different target nucleic acid). For example, the color or type of the reporter group is associated with a specific target. Thus multiple sets of target specific nucleic acids can be used to assay different targets simultaneously with the different colors seen under the microscope (or via other detection methods) being associated with the presence of the different targets.

In one further embodiment where molecular post binding and/or detection probe binding occurs after ligation, the methods of the invention further comprise forming a concentration gradient of ligation products prior to contacting the ligation products with the molecular post and/or detection probe. This embodiment accelerates the binding of the molecular post and/or detection probe to the ligation product. As used herein, the "concentration gradient" results in decreasing the surface area in which the ligation products are contained. This has the advantage that a larger volume of a dilute sample can be examined with the result that only a small area must be searched to find the evidence of the ligation product. This results in concentrating the ligation product in a dilute solution.

In a further embodiment a small area of the surface has a high affinity to bind the ligation product. As the droplet of sample is positioned over the surface, the affinity for the ligation product removes the ligation product from the solution, thereby creating a concentration gradient. The high affinity binding surface may be surrounded by a low affinity surface, such as a hydrophobic area, to enhance the concentrating effect by restricting the size of the droplet to surface interaction.

In a specific embodiment, forming the concentration gradient comprises providing a hydrophobic surface (including but not limited to silane coated surface, lagmuir-blogett films, etc.), and placing a small volume of a hydrophilic solvent (which can be any solvent that has a hydrophobicity opposite that of the surface, including but not limited to water, buffered solutions, saline, etc.) containing the ligation products on the hydrophobic surface, which creates a concentration gradient through surface tension effects to direct the ligation products to the edge of the surface and the bubble. This increases the amount of ligation product at the surface edge, resulting in a decreased time of detection through improved molecular post binding and/or detection probe binding.

As will be understood by those of skill in the art, a hydrophilic surface and a hydrophobic solvent can be used in an alternative embodiment to accomplish the same goal of forming the concentration gradient.

Any volume of solvent that is suitable for the intended purpose can be used. The determination of a solvent volume appropriate for a given application is well within the level of those of skill in the art.

Other methods for forming the concentration gradient include, but are not limited to, drying the volume of solvent on the hydrophobic surface, and utilizing a semi-permeable membrane.

Figure 4:
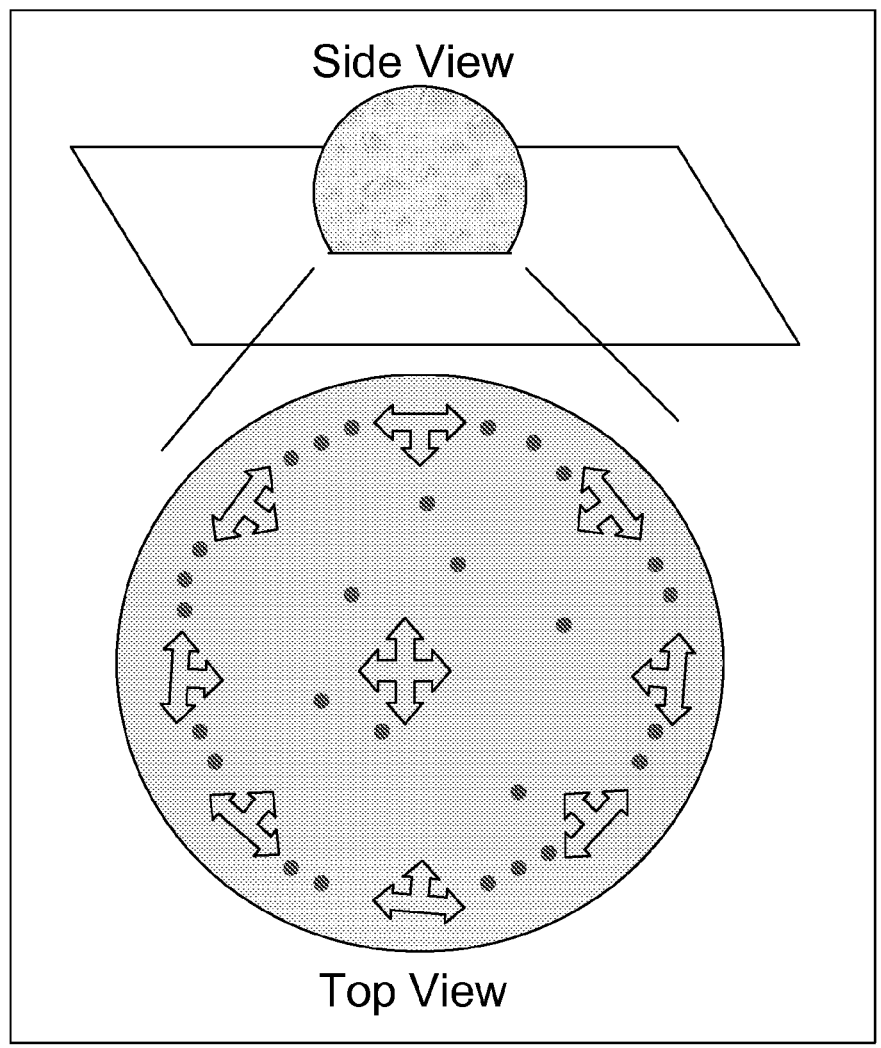
FIG. 4. Schematic of additional embodiment using magnetic particles.
Figure 5:
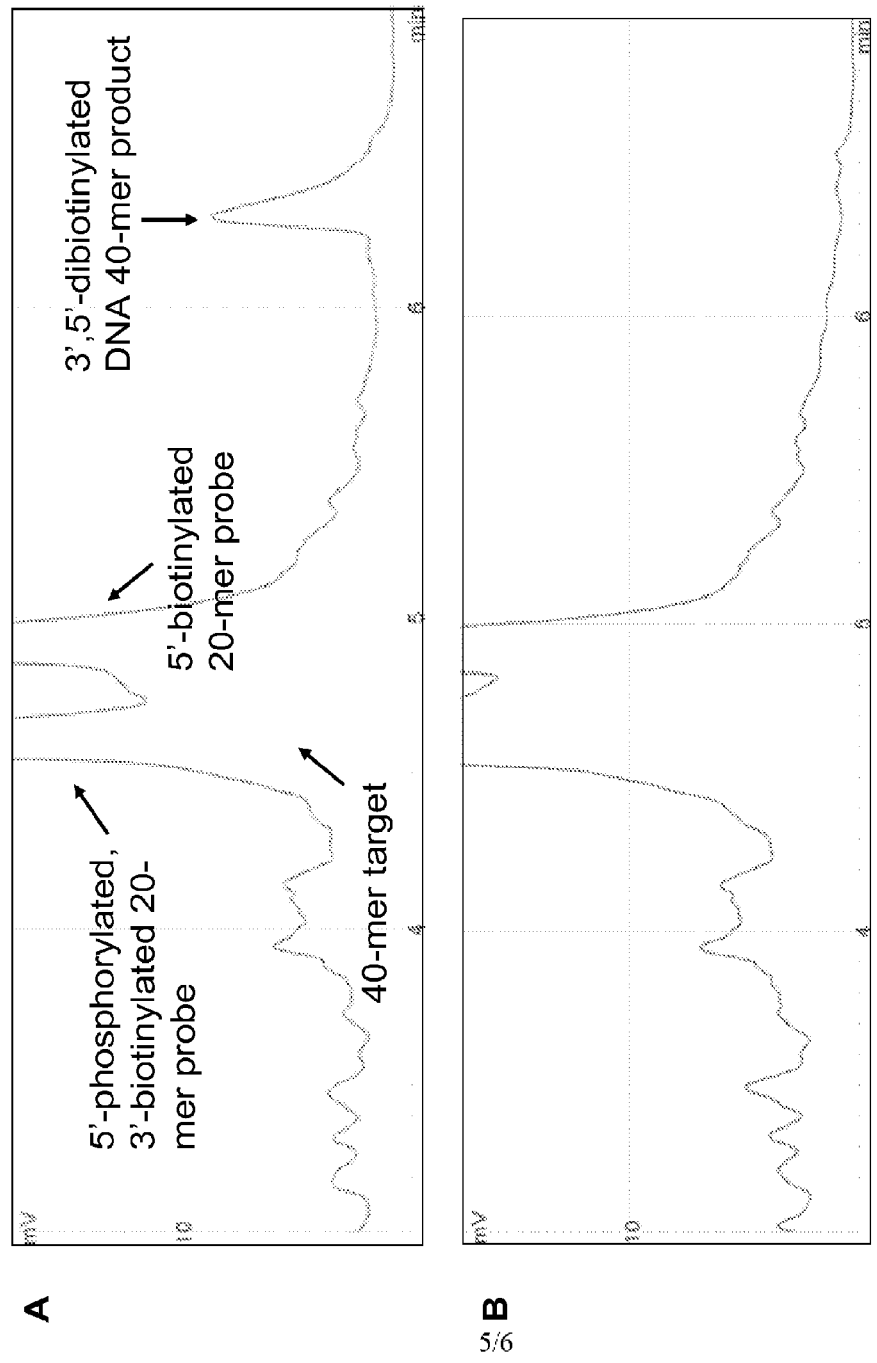
FIG. 5A-B. HPLC results demonstrate the specificity of ligase during the first step of LXR.
Figure 6:
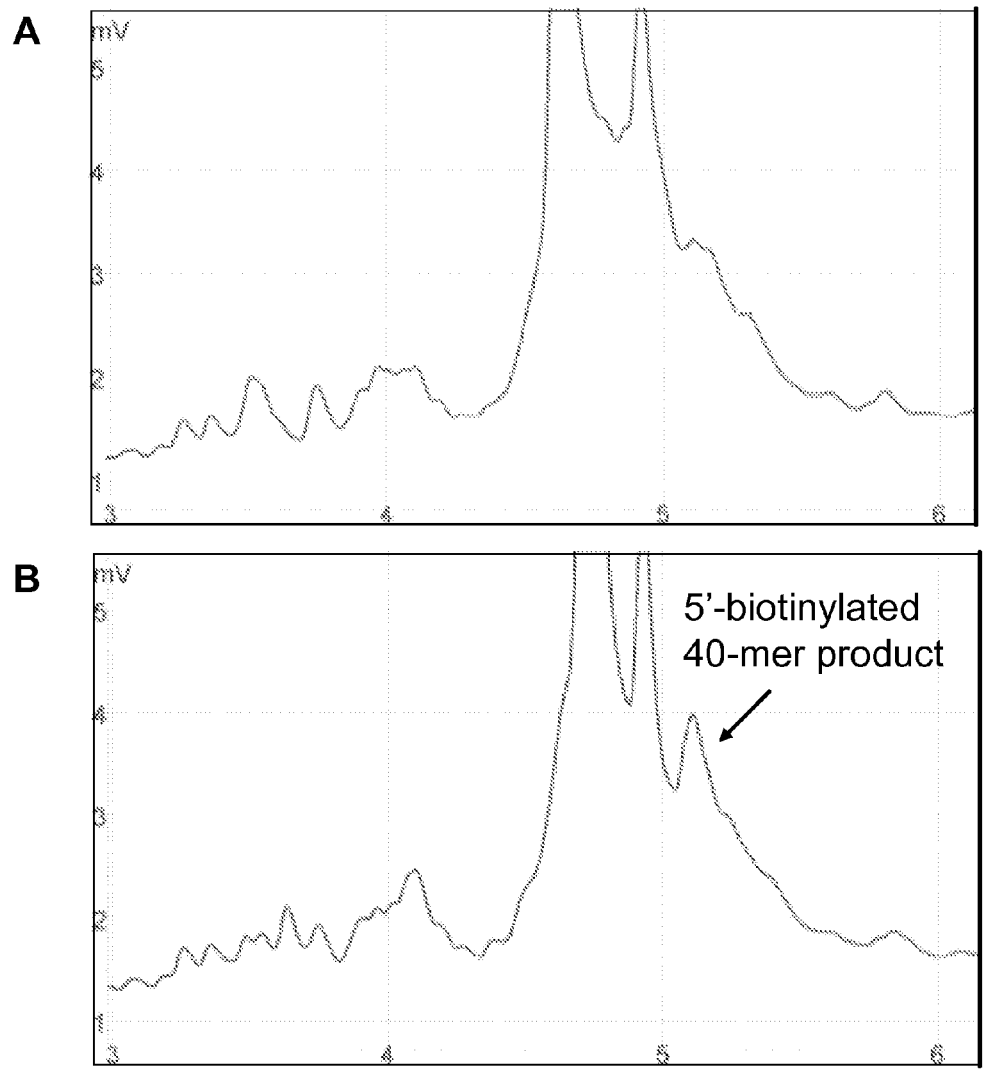
FIG. 6A-B. HPLC results demonstrate the specificity of exonuclease during the second step of LXR.

FIG. 4 provides an example of forming a concentration gradient.

Use of the concentration gradient provides more rapid binding and a higher percentage of ligation products bound to the detection probe/posts per unit time, thus improving the speed of the overall methods. Furthermore, use of the concentration gradient decreases the error rate significantly, by providing a localized area of detection with a more controllable readout area.

The present invention offers significant improvements over previous nucleic acid detection techniques. First of all, there is no requirement for an enzyme or biomolecular motor which is difficult to maintain. Second, the present invention provides much more controlled conditions than are possible when using an enzyme to generate movement. The invention herein allows a magnetic field to induce movement of bound particles, thereby still differentiating specifically bound probes by moving the particles significant distances.

In another aspect, the present invention provides kits for nucleic acid detection comprising a plurality of target-specific nucleic acid probes that are each complementary to a target nucleic acid, wherein upon hybridization to the target nucleic acid the plurality of target-specific nucleic acid probes will be directly adjacent to each other; wherein a first target specific nucleic acid probe is capable of binding or is bound to a molecular post and a second target-specific nucleic acid probe is capable of binding or is bound to a detection probe, and wherein the first target-specific nucleic acid probe and the second target-specific nucleic acid probe are positioned at the 5' and 3' end, respectively, of the series of target specific nucleic acid probes. As used in this aspect of the invention, terms carry the same meanings as for previous aspects of the invention.

In further specific embodiments, the first target-specific nucleic acid probe is capable of binding to a molecular post, and/or the second target-specific nucleic acid probe is capable of binding to the detection probe, and the kit further comprises a molecular post that binds to the first target-specific nucleic acid probe and/or a detection probe that binds to the second target-specific nucleic acid probe. In a further embodiment, the molecular post is bound to a solid support, such as a glass coverslip or other suitable support. The support can be derivatized in any manner suitable for binding to the molecular post. In a specific embodiment, the molecular post comprises a magnetic particle.

The present invention also provides a composition comprising a plurality of target-specific nucleic acid probes that are each complementary to a target nucleic acid, wherein upon hybridization to the target nucleic acid the plurality of target-specific nucleic acid probes will be directly adjacent to each other; wherein a first target specific nucleic acid probe is bound to a first affinity tag capable of binding to a molecular post and a second target-specific nucleic acid probe is bound to a second affinity tag capable of binding to a detection probe, and wherein the first target-specific nucleic acid probe and the second target-specific nucleic acid probe are positioned at the 5' and 3' end, respectively, of the series of target specific nucleic acid probes. In a further embodiment, the plurality of target-specific nucleic acid probes is ligated together.

The present invention also provides a composition comprising:
(a) a nucleic acid complex comprising a plurality of target-specific nucleic acid probes that are each complementary to a target nucleic acid, wherein upon hybridization to the target nucleic acid the plurality of target-specific nucleic acid probes will be directly adjacent to each other; wherein a first target specific nucleic acid probe is bound to a first affinity tag capable of binding to a molecular post and a second target-specific nucleic acid probe is bound to a second affinity tag capable of binding to a detection probe, and wherein the first target-specific nucleic acid probe and the second target-specific nucleic acid probe are positioned at the 5' and 3' end, respectively, of the series of target specific nucleic acid probes, and wherein the series of target-specific nucleic acid probes are ligated together;
  (b) a molecular post bound to the first affinity tag; and
  (c) a detection probe bound to the second affinity tag.

The present invention further provides a composition comprising:
  (a) a solid support; and
  (b) a plurality of molecular posts attached to the solid support, wherein the plurality of molecular posts comprise an affinity target for binding to a specific affinity tag. In a specific embodiment, the molecular posts comprise magnetic particles.

In a specific embodiment, the plurality of molecular posts comprises more than one type of molecular post. In a further specific embodiment, the different types of molecular posts on the support comprise different affinity targets that are specific for different affinity tags. In a further specific embodiment, the composition further comprises a first target-specific nucleic acid bound to a first affinity tag that binds to the affinity target on the molecular post. In a further specific embodiment, the first target specific nucleic acid probe is hybridized to a target nucleic acid, and the target nucleic acid is further hybridized to a second target-specific nucleic acid probe that is bound to a second affinity tag, wherein the second affinity tag is bound to a detection probe.

EXAMPLES

Example 1

Two different target nucleic acids, WT and MT, which differ by one nucleotide, were tested with two different sets of target-specific nucleic acid probes. For each of the two target nucleic acids, the LXR reactions detailed in FIG. 1 were performed with target-specific nucleic acid probes denoted with a + or with target-specific nucleic acid probes containing an SNP denoted with a –. The amount of bridge formed under each of the four conditions was quantified by counting assembled devices (ligation products) containing the DNA bridge with F1 (molecular post) and nanogold (detection probe). The number of assembled devices is shown in FIG. 2 on the y-axis, where a comparison between the amount of binding for the WT and MT targets with both complementary target-specific nucleic acid probes and SNP target-specific nucleic acid probes is shown as the percent increase in binding.

For experiments in which LXR products prepared from purified target DNA were used for detection, target DNA, 3'-biotinylated capture probe (target-specific nucleic acid), and 5'biotinylated capture probe phosphorylated at the 3' end (target-specific nucleic acid) were allowed to hybridize, and the capture probes were ligated in the presence of 5,000 units of T4 ligase, T4 ligase buffer (New England Biolabs), 4 mM ATP, and 4 mM DTT in a final volume of 50 µl. After ligation, 35 µl of the product was incubated with 5,000 units of Phi 29 DNA polymerase, which has strong exonuclease activity, Phi 29 buffer (New England Biolabs), 2 mM dNTP, and BSA in a 50 µl total volume. To bind DNA bridges to the immobilized avidinated $F_1$-ATPase, a 3 µl droplet of either LXR product, 3',5'-dibiotinylated-DNA, or 3'-biotinylated-DNA was added to the cover slip at concentrations indicated such that the droplet was within the surface area to which avidinated $F_1$-ATPase was bound, and incubated for 10 min followed by a buffer wash.

Nanodevice assembly was completed by addition of 10 µl of nanorods, prepared as known in the art, in a droplet that covered the entire surface to which avidinated $F_1$-ATPase had become bound, and incubated for 10 min, then washed thoroughly in $F_1$-ATPase buffer to minimize nonspecifically bound nanorods. This allowed the avidin-coated gold nanorods to bind to the $F_1$-ATPase-immobilized, biotinylated DNA bridges. For samples that were examined for rotation, the final buffer contained 0.5 mM $MgCl_2$ and 1 mM ATP.

Figure 2:
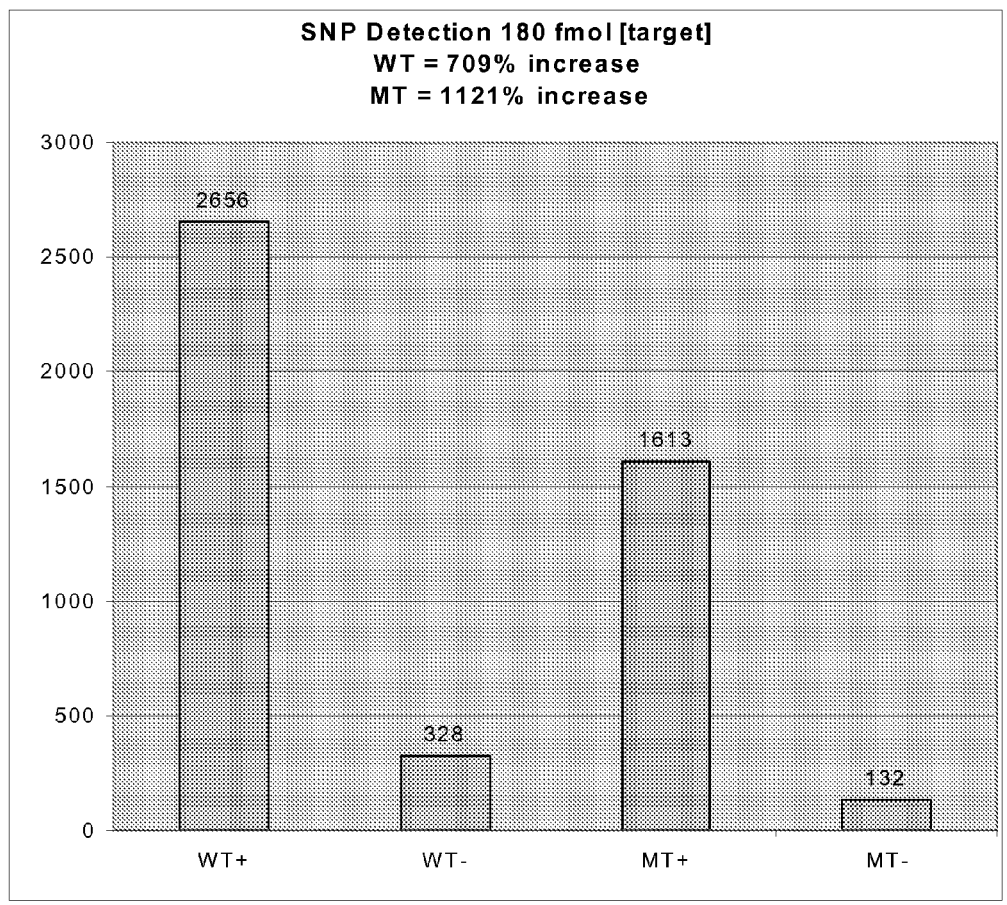
FIG. 2. Single Nucleotide Polymorphism detection using the LXR reaction.

FIG. 2 shows that the method is able to detect as few as 600 molecules of target DNA, and is able to distinguish target bound detection probes from those that are non-specifically bound.

Example 2

The conditions used in this example are the same as in the first example, but the data were analyzed via the HPLC rather than on the microscope. Biotinylated 20-mer oligonucleotide probes were mixed with a 40-mer target and allowed to ligate. Samples were then viewed with high performance liquid chromatography (HPLC) where each component corresponds to a distinct signal peak. When probes were complementary with the target at the site of ligation, a significant 3',5'-dibiotinylated 40-mer product peak formed as seen in (A). When there was a single mismatch at the site of ligation, no product was formed (B). Thus, HPLC results demonstrate the specificity of ligase during the first step of LXR.

After ligation, samples were subjected to exonuclease (phi-29 DNA polymerase) treatment. In the case of a mismatch during ligation, the presence of a nick allowed exonuclease to bind and extend the downstream probe, displacing the 3' biotin. This resulted in the formation of a significant 5'-biotinylated 40-mer product as seen by HPLC (A). If ligation was successful in the case of a perfect match at the ligation site, no significant 5'-biotinylated 40-mer product was formed by exonuclease (B). Thus, HPLC results demonstrate the specificity of exonuclease during the second step of LXR.

Example 3

FIG. 4 shows an embodiment of the methods using magnetic particles. A side view of the droplet on the surface is depicted at the top of the figure; molecules at the edge of the droplet have the fewest degrees of freedom, they may curve up along the edge of the droplet, move along the surface, or move out into the middle of the droplet. Those molecules that go to the surface are pulled out of solution as they bind. This creates a concentration gradient that pulls more molecules to the edge as shown in the top view. Molecules in the middle of the droplet are able to move in any direction; there is no preference to move toward or away from the surface. Thus the concentration gradient formed at the edge of the droplet and the surface is a dominating force, resulting in a significant percentage of all the molecules binding at the edge.

We claim:

1. A method for detecting a target nucleic acid, consisting essentially of:
   (a) contacting a plurality of target-specific nucleic acid probes that are each complementary to a target nucleic acid, to a sample under conditions whereby the plurality of target-specific nucleic acid probes hybridize to the target nucleic acid if the target nucleic acid is present in the sample, wherein upon hybridization to the target nucleic acid, the target-specific nucleic acid probes form a series of target-specific nucleic acid probes directly adjacent to one another, wherein a first target specific nucleic acid probe is capable of binding or is bound to a molecular post and a second target-specific nucleic acid probe is capable of binding or is bound to a detection probe, and wherein the first target-specific nucleic acid probe and the second target-specific nucleic acid probe are positioned at the 5' and 3' end, respectively, of the series of target specific nucleic acid probes;
   (b) binding the molecular post to the first target-specific nucleic acid probe and/or binding the detection probe to the second target-specific nucleic acid probe if the molecular post and/or detection probe were not bound prior to hybridization;
   (c) ligating the series of target-specific nucleic acid probes together to produce a ligation product;
   (d) after ligating then binding the molecular post to the first target-specific nucleic acid probe and/or binding the detection probe to the second target-specific nucleic acid probe and forming a concentration gradient of ligation products prior to contacting the ligation products with the molecular post and/or detection probe;
   (e) treating the ligation product with one or both of:
      (i) exonuclease digestion; and
      (ii) denaturation to create all single stranded bridges after ligation;
   (f) binding the molecular post to the first target-specific nucleic acid probe and/or binding the detection probe to the second target-specific nucleic acid probe if the molecular post and/or detection probe were not bound prior to the step (e) treatment; and
   (g) then detecting the ligation product.

2. The method of claim 1, wherein the step (e) treatment comprises exonuclease digestion.

3. The method of claim 1, wherein the step (e) treatment comprises denaturation.

4. The method of claim 1 wherein the plurality of target specific nucleic acid probes comprises at least 3 target specific nucleic acid probes.

5. The method of claim 1 wherein the plurality of target specific nucleic acid probes comprises at least 5 target specific nucleic acid probes.

6. The method of claim 1 wherein the ligation comprise ligation chain reaction.

7. The method of claim 1, wherein the molecular post comprises a magnetic particle.

8. The method of claim 7, further comprising applying a magnetic field to move the ligation product.

9. The method of claim 1 wherein the molecular post is immobilized for detection.

10. The method of any claim 1, wherein the detecting comprises fluorescence microscopy, surface plasmon resonance, gel electrophoresis, calorimetric shifts, electric conductivity or autoradiography.

11. The method of claim 1 wherein the sample is selected from the group consisting of synthetic nucleic acids, genomic DNA, cell lysates, tissue homogenates, forensic samples, environmental samples, and isolated nucleic acid samples.

12. The method of claim 1 wherein the target nucleic acid comprises double stranded DNA.

* * * * *